US005267983A

United States Patent [19]

Oilschlager et al.

[11] Patent Number: 5,267,983
[45] Date of Patent: Dec. 7, 1993

[54] ENTERAL ADAPTER AND TIP PROTECTOR

[75] Inventors: Edward G. Oilschlager, North Chicago; Thomas R. Lillegard, Crystal Lake, both of Ill.

[73] Assignee: Clintec Nutrition Co., Deerfield, Ill.

[21] Appl. No.: 872,787

[22] Filed: Apr. 22, 1992

[51] Int. Cl.[5] A61M 3/00
[52] U.S. Cl. 604/283; 604/256
[58] Field of Search 604/243, 256, 283, 905, 604/326; 128/912; 285/177

[56] References Cited

U.S. PATENT DOCUMENTS

| | | | |
|---|---|---|---|
| D. 283,442 | 4/1986 | Richmond . | |
| D. 283,641 | 4/1986 | Spetzler et al. . | |
| 3,741,217 | 6/1973 | Ciarico | 604/283 |
| 3,835,862 | 9/1974 | Villari | 604/256 |
| 4,013,064 | 3/1977 | Patel et al. | 604/326 |
| 4,270,778 | 6/1981 | Brownell | 604/283 |
| 4,511,163 | 4/1985 | Harris et al. . | |
| 4,731,061 | 3/1988 | Matkovich | 604/256 |
| 4,950,254 | 8/1990 | Andersen et al. | 604/256 |
| 4,969,879 | 11/1990 | Lichte . | |
| 5,049,139 | 9/1991 | Gilchrist . | |
| 5,057,093 | 10/1991 | Clegg et al. . | |

FOREIGN PATENT DOCUMENTS

| | | | |
|---|---|---|---|
| 0636526 | 6/1983 | Switzerland | 604/256 |

*Primary Examiner*—John D. Yasko
*Assistant Examiner*—Anthony Gutowski
*Attorney, Agent, or Firm*—Hill, Steadman & Simpson

[57] ABSTRACT

A multi-stepped adapter for accommodating a wide range of diameters of access ports of enteral feeding devices. The leading step of the adapter is sized in length and diameter to prevent a secure connection to an IV access port, such as an intravenous needle or luer connection.

24 Claims, 1 Drawing Sheet

ENTERAL ADAPTER AND TIP PROTECTOR

BACKGROUND OF THE INVENTION

The present invention relates generally to adapters for mating a fluid source with a delivery tube. More particularly, the present invention relates to adapters for connecting an enteral fluid source to an enteral feeding device.

It is known to infuse nutritional formulations into a patient. Such nutritional products can be administered either enterally or parenterally. One enteral means for providing such nutrition is by use of a feeding tube which is connected to a supply or source of a liquid nutritional product. Likewise, one means for providing intravenous solution to a patient is by use of an IV needle. The IV needle is inserted into a patient's venous system. A luer fit or connection allows an adapter or coupler to be secured therein so that fluid can be infused through the needle into the patient.

For example, it is known to insert a catheter into a patient percutaneously or to use a nasogastric feeding tube. The catheter, or tube is connected to a container holding a liquid nutritional product via a fluid conduit. Various size adapters are normally provided at an outlet end of the fluid conduit. The adapters frictionally fit into an open end of the feeding catheters, or tube.

An example of such an adapter is a multi-step adapter disclosed in U.S. Pat. No. 5,057,093. Stepped adapters provide the advantage that an outer surface provides a series of stepped surfaces of progressively smaller diameters from the flow inlet of the adapter to the flow outlet of the adapter. Thus, the adapter can be inserted into a wide variety of feed tubes and catheters of varying diameters and depths. Such adapter, however, also present the problem of allowing one to inadvertently insert the adapter into an IV luer fit or access port. This can allow one to accidentally introduce fluid into a patient's venous system. Of course, liquid formulas designed to be introduced into a patient's gastro/intestinal tract cannot be introduced into a patient's venous system without harmful consequences to the patient.

Because the diameter size for a standard IV access port is similar to the diameters of some small enteral access ports, universal enteral adapters, i.e. adapters that are designed to fit a variety of enteral feed tubes, can be inadvertently inserted into an IV luer access port. In this regard, an IV access port or luer connection is typically a port with an approximate diameter of 0.170", and having tapered sidewalls for securing an adapter therein. Universal enteral adapters typically have a small diameter tip section, approximately 0.175" diameter, so that the adapter can be used for small enteral access ports. Thus, the potential exists that the enteral adapter can accidentally be inserted and secured to an IV luer connection.

SUMMARY OF THE INVENTION

The present invention provides an effective multi-step universal adapter for an enteral feed tube. The tip or leading section the adapter has a combined diameter and length that prevents secure attachment of the adapter to a standard size IV luer connector or fit.

The overall length of the multi-step adapter has been minimized and yet a land area on each step is provided that ensures a leak proof seal for a wide range of mating enteral feeding tubes. Each step uses a specific radius to allow for insertion into enteral feeding tubes without lubricants. The radii and step diameters of the adapter allow for the use of five steps instead of the traditional four steps.

The base of the adapter provides a flange that is designed to be flat on one surface for ease of location and transfer of parts for automation equipment during manufacture. The opposite side of the flange provides a slot on two sides with raised tabs on either side of each slot to lock a tethered mating tube cap, stretched from its connection to the feed tube, to the adapter. This holds the adapter to the enteral access port tube of the feed tube.

An adapter tip protector or sheath is provided that is designed specifically for use with the above-described adapter. The tip protector provides an internal ribbing structure which serves two functions. The ribs are spaced and designed to provide for easy removal of the tip protector with a specific assembly and removal force. The rib design also provides a sterilization path for gas sterilization and a potential sterile barrier. The external design of the tip protector has linear protrusions to allow a twisting motion to be used for removal and enhance the compression strength of the tip.

The enteral adapter can be color coded red which indicates enteral use only to those skilled in the art.

Additional features and advantages of the present invention are described in, and will be apparent from, the detailed description of the presently preferred embodiments and the drawings.

DETAILED DESCRIPTION OF THE PRESENTLY PREFERRED EMBODIMENTS

The present invention provides a universal enteral adapter that will fit a wide variety of enteral feed tubes. However, the enteral adapter will not allow an IV needle to be securely attached to the adapter.

Figure 1:
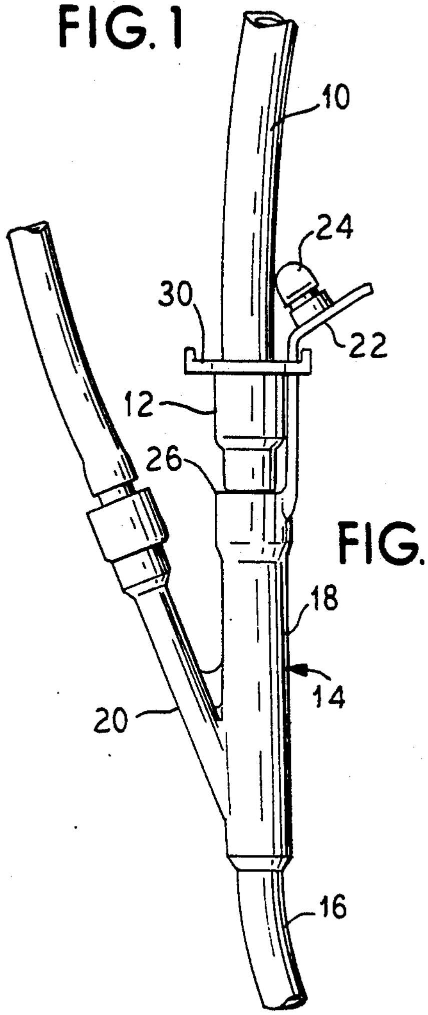
FIG. 1 illustrates a front perspective view of an adapter of the present invention inserted into an enteral access port feed tube.

Referring now to the figures, and specifically FIG. 1, a first fluid conduit 10 attached to an adapter 12 is illustrated. The fluid conduit 10 is connected to an enteral fluid source, e.g. bag. The adapter 12, as illustrated, is attached to an enteral feed tube 14 that communicates into a second fluid conduit 16 which leads into a patient's gastro/intestinal system. This allows fluid from the container to be infused into a patient.

The illustrated feed tube 14 includes a "y" type connector that provides a primary access port 18 and a secondary access port 20. In the illustrated example, the primary access port 18 provides a tethered closure cap 22 which has a stopper 24, which can be bent down to be inserted into a primary access hole 26 to close the primary access port 18 when not in use. Of course other types of enteral tubes can be used with the present invention.

When the adapter 12 is in place in the primary access aperture 26 of the feed tube 14, the tethered access cap 22 can be stretched upward and resiliently engaged into a slot 28 (shown in FIG. 3) formed in a flange 30 of the adapter 12. The tethered cap 22 thus acts as a strap retainer to hold the adapter 12 together with the primary access port 18.

Figure 2:
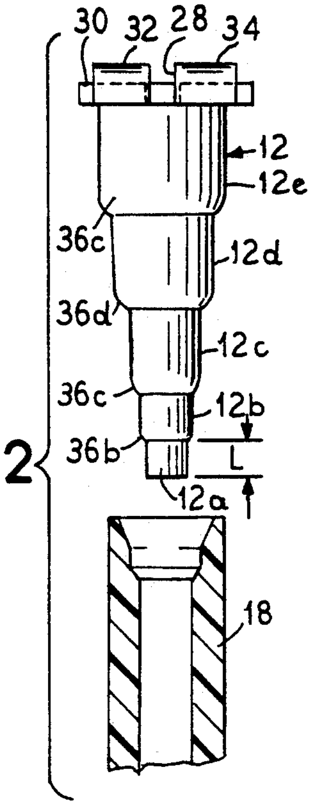
FIG. 2 illustrates a partial exploded view of the adapter of FIG. 1 and an enteral feed tube shown in section.

As illustrated in FIG. 2, the adapter preferably comprises five sequential stepped diameters, forming five cylinder sections 12*a*, 12*b*, 12*c*, 12*d* and 12*e*, in increasing diameter order. In the presently preferred embodiment, a first section 12*a* has length of approximately 0.14" and a diameter of 0.162"±0.003"; a second section 12*b* has a length of approximately 0.16" and a diameter of approximately 0.195"; a third section 12*c* has a length of approximately 0.29" and a diameter of approximately 0.25"; a fourth section 12*d* has a length of approximately 0.32" and a diameter of approximately 0.36"; and a fifth section 12*e* has a length of approximately 0.39" (not including the flange 30) and a diameter of approximately 0.44".

On a back side of the fifth section 12*e* is mounted the flange 30 having the slots 28 therein. The slots 28 provide tabs 32, 34 on opposite sides of the slot 28 which assist in securing the tethered access cap within the slot 28.

Each of the sections 12*b* through 12*e* includes on a leading end thereof a rounded transition section 36*b*, 36*c*, 36*d* and 36*e* respectively. These rounded transition sections allow for smooth and easy insertion of the adapter into an access port without the use of lubricant.

An important aspect of the invention is the dimensioning of the first segment 12*a*. In accordance with the present invention, by dimensioning the first section 12*a* to have a length L equal to approximately 0.14" with a diameter of approximately 0.162±0.003" the adapter cannot be erroneously secured into an IV luer. Although an IV luer has a diameter that will allow it to accept a 0.162" diameter tube, the adapter will not be securely received within a standard IV luer because it is only approximately 0.14" long. Instead of being securely received therein, as some currently used commercial enteral adapters may, the adapter 12 will fall out of the IV luer connector.

The next section 12*b* of the adapter 10 has a diameter of approximately 0.195". This diameter prevents this section 12*b* from being inserted into a s IV or luer connection.

In comparison, the prior art adapters have a lead segment with a diameter of approximately 0.175" and a length of approximately 0.3". The length of a standard adapter is long enough and thick enough to insert into an IV or luer port and be gripped therein by the tapered inside walls of the IV or luer port.

Figure 3:
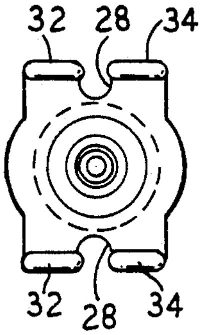
FIG. 3 illustrates a top plan view of the adapter of FIG. 2.
Figure 4:
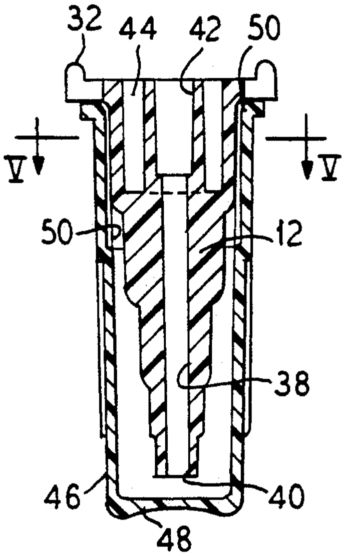
FIG. 4 illustrates a sectional view of the adapter of FIG. 2 inserted into a tip protector.

FIGS. 3 and 4 illustrate the inside of the adapter 12 which has a central channel 38 having a discharge opening 40 at a first end, or at a lead end thereof, and an inlet opening 42 at a back end thereof. The back end thereof is fashioned to attach a tube 10 such as shown in FIG. 1. To this end, tube 10 is inserted into an annular channel 44 formed at a back end of the adapter.

In use, a fluid conduit 10 of an enteral fluid container will be secured to the enteral adapter 12. Due to the construction of the adapter 12, the adapter 12 will allow the fluid container to be placed in fluid communication with effectively any type of NG enteral feeding devices.. as well as G-tubes or J-tubes. However, the adapter 12 will prevent a healthcare personnel from inadvertently placing the enteral container in fluid communication with an IV luer.

Figure 8:
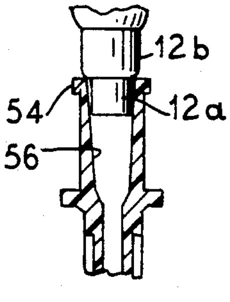
FIG. 8 illustrates a partial sectional view of the adapter of FIG. 1 being erroneously inserted into an IV or luer port.

As illustrated in FIG. 8, if the adapter 12 is inadvertently inserted into a luer or IV port 54, although the first section 12*a* is received in the port 54 it is too short and narrow to be gripped by the tapered walls 56 of the port 54. The luer port 54 is also too rigid to open up to accept the fourth sect 12*b* which has a diameter of 0.195", therefore the adapter 12 will fall out.

Figure 5:
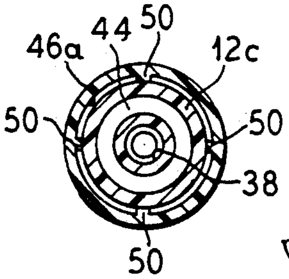
FIG. 5 illustrates a sectional view taken generally along lines V—V of FIG. 4.

FIG. 4 illustrates a tip protector 46 installed onto the adapter 12. The tip protector 46 has a closed leading end 48 and an opened trailing end 50. Inside the tip protector 46 are four ribs 50 arranged at quarter points around a circle as illustrated in FIG. 5. Once the adapter 12 is inserted into the cap 46 the ribs 50 resiliently grip and space the fifth section 12*e* from an inside diameter of the tip protector 46*a* providing pathway for gas sterilization of the adapter 12 retained in the protector 46.

The ribs allow the tip protector to have a sufficient removal force to function satisfactorily. To this end, the following experiment was performed:

Assembled enteral adaptor tip protector were placed over universal enteral adapters of the present invention. 12 assembled units were placed into environmental chamber set at 147° F. for a period of 10 days (heat aging). One group of four remained as a control (one from each cavity).

Tip protector removal force was determined using Amtek force gauge with 20" per minute pull rate.

RESULTS

| Tip Cavity No. | Enteral Adapter Cavity No. | Force Required in Pounds |
|---|---|---|
| Control | | |
| 1 | 1 | 2.5 |
| 2 | 2 | 3.7 |
| 3 | 4 | 2.0 |
| 4 | 3 | 3.4 |
| Mean - 2.9 pounds | | |
| Std. Dev. - .6819 | | |
| Heat Aged Units | | |
| 1 | 2 | 3.8 |
| 1 | 1 | 2.9 |
| 1 | 3 | 3.1 |
| 2 | 2 | 3.9 |
| 2 | 3 | 3.8 |
| 2 | 4 | 2.8 |
| 3 | 1 | 3.5 |
| 3 | 3 | 3.2 |
| 3 | 4 | 3.5 |
| 4 | 2 | 3.0 |
| 4 | 1 | 3.4 |
| 4 | 4 | 3.0 |
| Mean - 3.325 pounds | | |
| Std. Dev. - .3631 | | |
| Performed Removal of Tip on Competitive Enteral Set | | |
| | 7.1 pounds | |
| | 7.5 pounds | |
| | 8.2 pounds | |
| | Mean - 7.6 pounds | |
| | Std. Dev. - .4546 | |

The above experiment demonstrates that the construction of the tip protector 46 allows it to have a sufficient removal force when used on the enteral adapter 12 of the present invention.

Figure 6:
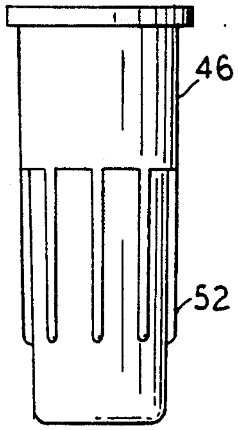
FIG. 6 illustrates a front elevational view of the tip protector shown in FIG. 4.
Figure 7:
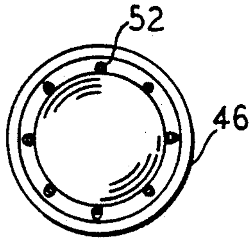
FIG. 7 illustrates a bottom plan view of the tip protector of FIG. 6.

As illustrated in the preferred embodiment of the tip protector 46 of FIGS. 6 and 7, a plurality of external ribs 52 are located around a perimeter of the tip protector 46. The ribs 52 strengthen the tip protector 46. Additionally, the ribs 52 provide a finger gripping surface for removing the protector from the adapter 12 by twisting.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim as our invention:

1. A universal enteral adapter for connecting an enteral fluid source to a variety of enteral feed tubes having varies sized access ports comprising:

a body having a channel therethrough, defining a first opening at a first end and a second opening at a second end, the body having a first cylindrical section adjacent the first opening having a diameter of less than approximately 0.170" and a second cylindrical section adjacent the first cylindrical section on a side opposite the first opening, and a transition section between the first cylindrical section and the second cylindrical section, the second cylindrical section having portions extending to an outside dimensional diameter of greater than approximately 0.170" so as to prevent the adapter from being secured within an opening of the standard IV luer, the body including means for coupling an enteral fluid source to the body, located proximate the second opening.

2. The adapter of claim 1 wherein the body further comprises a third cylindrical section axially adjacent the second cylindrical section on a side opposite said first cylindrical section, and a second rounded transition section between the second cylindrical section and said third cylindrical section.

3. The adapter of claim 1 wherein the body comprises a plurality of additional cylindrical sections in sequence, arranged axially adjacent said second cylindrical section on a side opposite said first cylindrical section, and a plurality of rounded transition sections, one arranged between each adjacent pair of cylindrical sections.

4. An adapter for connecting an enteral source to an enteral feed tube comprising:

a body defining a channel axially disposed therethrough, having a first opening at a first end and a second opening;

means for allowing the adapter to be securely received within an aperture of a number of different sized openings of enteral feed tubes, said means including said body having a region adjacent said first end having an overall taper, and at said first end having a first section having a first diameter of less than approximately 0.170" and a first length of less than or equal to approximately 0.14", said first section connected to a second section having a second diameter greater than said first diameter said first and second diameters sized for said first and second sections to be insertable into said number of different sized openings of enteral feed tubes, the body including means for connecting an enteral fluid source, the means being located proximate the second opening.

5. The adapter of claim 4 wherein the body first section comprises a first cylindrical section having a region of constant diameter.

6. The adapter of claim 4 wherein said first length is approximately 0.14".

7. The adapter of claim 4 wherein said first diameter is approximately 0.16".

8. The adapter of claim 5 wherein said second section comprises a second cylindrical section adjacent said first cylindrical section, said second cylindrical section having a constant diameter greater than a maximum diameter of said first cylindrical section.

9. The adapter of claim 4 wherein said first section comprises a first cylindrical section having a constant diameter, and said second section comprises a second cylindrical section having a constant diameter, and the body comprises a third, fourth and fifth cylindrical sections having increasing diameter from said second cylindrical section toward said second opening.

10. The adapter of claim 8 wherein said second cylindrical section comprises a rounded transition portion merging said second cylindrical section into said first cylindrical section.

11. The adapter of claim 4 wherein said body includes an outwardly extending flange at said second opening, said flange having opposing flat sides and at least one slot for receiving a portion of the enteral feed tube.

12. An adapter for connecting an enteral fluid source to an enteral feed tube comprising:

a body having a channel therethrough defining a first opening at a first end and a second opening at a second end, said body providing in sequential order from said first end to said second end, a first cylindrical segment having a diameter of less than approximately 0.170", a second cylindrical segment having a diameter of greater than approximately 0.170", a third cylindrical segment, a fourth cylindrical segment, and a fifth cylindrical segment, said cylindrical segments being arranged in increasing stepped diameters from said first cylindrical segment to said fifth cylindrical segment wherein said second and third cylindrical segments include at a respective lead end thereof a rounded transition segment, the body including means for connecting an enteral fluid source tube, located proximate the second opening.

13. An adapter for connecting an enteral fluid source to an enteral feed tube comprising:

a body having a channel therethrough defining a first opening at a first end and a second opening at a second end, said body providing in sequential order from said first end to said second end, a first cylindrical segment, a second cylindrical segment, a third cylindrical segment, a fourth cylindrical segment, and a fifth cylindrical segment, said cylindrical segments being arranged in increasing stepped diameters from said first cylindrical segment to said fifth cylindrical segment wherein the first cylindrical segment includes a diameter less than approximately 0.175" and a length of less than or equal to approximately 0.14", and the second cylindrical segment comprises a diameter of greater than approximately 0.175", the body including means for connecting an enteral fluid source located proximate the second opening.

14. An adapter for connecting an enteral fluid source to an enteral feed tube comprising:

a body having a channel therethrough defining a first opening at a first end and a second opening at a second end, said body providing in sequential order from said first end to said second end, a first cylindrical segment, a second cylindrical segment, a third cylindrical segment, a fourth cylindrical segment, and a fifth cylindrical segment, said cylindrical segments being arranged in increasing stepped diameters from said first cylindrical segment to said fifth cylindrical segment wherein the first cylindrical segment includes a diameter less than approximately 0.16", the second cylindrical segment comprises a diameter of approximately 0.19", the third cylindrical segment comprises a diameter of approximately 0.25", the fourth cylindrical segment comprises a diameter of approximately 0.36" and the fifth cylindrical segment comprises a diameter of approximately 0.44", the body including means for connecting an enteral fluid source, the means being located proximal the second opening.

15. An enteral adapter for connecting an enteral fluid source to an enteral feed tube comprising:

a body having a channel axially disposed therethrough and having a first opening at a first end and a second opening at a second end, the body including a first region adjacent said first end having a length of approximately 0.14" and a diameter of less than 0.170 an increase in diameter at a second region adjacent said first region to greater than 0.170", and the second end including means for coupling an enteral fluid source thereto; and a flange member located on said body adjacent the second end, the flange member providing laterally opposed flat sides and including at least one slot.

16. The adapter of claim 15 wherein the slot is bounded by a formation to engage and hold a retaining strap of the enteral feed tube.

17. The adapter of claim 16 wherein the flange includes an outwardly extending tab.

18. An adapter for connecting an enteral fluid source to an enteral feed tube comprising:

a body having a channel axially disposed therethrough and having a first opening at a first end and a second opening at a second end, the body including a first section having a diameter of less than 0.170" and a second section having a diameter of greater than 0.170", the body including means for connecting an enteral fluid source to the second opening; and a flange member located on said body, the flange member providing laterally opposed flat sides and wherein the flange member is arranged at the second end of said body and provides two slots on opposing lateral sides, the slots each bounded by two tab members extending perpendicularly to the flange member.

19. A method for connecting an enteral feed tube to an enteral feed tube access port comprising the steps:

providing an adapter having an inlet port and an outlet port flow connected by a channel inside the adapter;

providing the adapter with a body section adjacent said outlet port, constructing the body section to be insertable and engageable into a variety of different diameter enteral access ports; and constructing the body section with a first section having a diameter of less than 0.170" and a length of approximately 0.14" to be partly insertable into a standard IV luer having a diameter of 0.170" but also including a second section having a diameter of greater than 0.170" to prevent the adapter from being inadvertently secured within a standard IV luer;

securing the enteral feed tube to the inlet port of the adapter;

inserting the body section of the adapter adjacent the outlet port into the enteral feed tube access port.

20. The method of claim 19 wherein the step of constructing is characterized by: providing the adapter with a body portion insertable into the stand IV luer but that is too short to be gripped by the standard IV luer.

21. An enteral adapter for connecting an enteral fluid source to an enteral feed tube and tip protector comprising:

a body having a channel therethrough defining a first opening at a first end and a second opening at a second end, said body providing in sequential order from said first end to said second end, a first cylindrical segment, a second cylindrical segment, a third cylindrical segment, a fourth cylindrical segment, and a fifth cylindrical segment, said cylindrical segments being arranged in increasing stepped diameters from said first cylindrical segment to said fifth cylindrical segments, said first segment having a first diameter of less than approximately 0.14 said second segment having a diameter of greater than approximately 0.170" said first and second segments insertable into a standard enteral port of an enteral feed tube, and means for coupling an enteral fluid source to the second end of the body; and a tip protector for removably covering the adapter, the tip protector defining an interior including a plurality of interior ribs.

22. The adapter and tip protector of claim 21 wherein the tip protector includes on an outer surface a plurality of exterior ribs.

23. The adapter and tip protector of claim 21 wherein the interior ribs are arranged longitudinally spaced apart to provide a lengthwise path for gas sterilization.

24. The adapter and tip protector of claim 21 wherein the interior ribs are sized having a height proceeding inwardly to cause said interior ribs to grip said fifth cylindrical section and to assure a predetermined removal force from the adapter.

* * * * *